United States Patent [19]

Freneix

[11] Patent Number: 5,774,568
[45] Date of Patent: Jun. 30, 1998

[54] METHOD OF TESTING A SURFACE NON-DESTRUCTIVELY IN PARTICULAR IN A HOSTILE ENVIRONMENT

[75] Inventor: Gérard Freneix, Saint Sebastien, France

[73] Assignee: GEC Alsthom Systemes et Services SA, Paris, France

[21] Appl. No.: 592,462

[22] Filed: Jan. 26, 1996

[30] Foreign Application Priority Data

Jan. 27, 1995 [FR] France ................................ 95 00962

[51] Int. Cl.[6] .................................................. G06K 9/00
[52] U.S. Cl. ........................ 382/100; 382/108; 382/153; 382/154; 364/507
[58] Field of Search .................................. 382/100, 108, 382/153, 154; 345/139; 395/135; 364/507; G06K 9/00

[56] References Cited

U.S. PATENT DOCUMENTS

| | | | |
|---|---|---|---|
| 4,642,687 | 2/1987 | Wedgewood et al. | 350/110 |
| 4,759,074 | 7/1988 | Iadiapaolo et al. | 382/23 |
| 4,847,510 | 7/1989 | Douglas | 356/371 |
| 4,969,106 | 11/1990 | Vogel et al. | 364/508 |
| 5,165,101 | 11/1992 | Cox et al. | 382/8 |
| 5,311,784 | 5/1994 | Girard et al. | 364/474.17 |
| 5,321,766 | 6/1994 | Fraas et al. | 382/8 |
| 5,353,356 | 10/1994 | Waugh et al. | 382/8 |
| 5,440,396 | 8/1995 | Markus et al. | 356/394 |
| 5,475,613 | 12/1995 | Itoga et al. | 364/507 |
| 5,590,170 | 12/1996 | Zweig | 378/63 |

OTHER PUBLICATIONS

West et al, "Image Processing and Understanding for Automatic Inspection", *Transaction of the Institute of Measurement and Control*, vol. 10, No. 5, 1 Oct. 1998, pp. 265–272.

*Primary Examiner*—Thomas L. Stoll
*Attorney, Agent, or Firm*—Sugrhue, Mion, Zinn, Macpeak & Seas, PLLC

[57] ABSTRACT

A method for obtaining data representing the physical dimensions of a physical three-dimensional object without actually measuring the dimensions of the object. The data is obtained by providing a video image of the object and a model data representing an ideal model of the object. The model data is used to construct a model image, which is then superimposed over the video image. The model data is then modified until the model image exactly overlaps the video image. At that point, the data as so modified represents the physical dimensions of the object. The method is particularly suitable for inspecting object and surfaces for defects, especially when human presence is not desired.

12 Claims, 2 Drawing Sheets

METHOD OF TESTING A SURFACE NON-DESTRUCTIVELY IN PARTICULAR IN A HOSTILE ENVIRONMENT

The present invention relates to a method of testing a surface non-destructively in particular in a hostile environment. The term "hostile environment" is used to mean any environment in which access to man is either impossible or very limited, e.g. space, the sea bed, or zones polluted by chemical, radioactive, or other polluting substances.

BACKGROUND OF THE INVENTION

In order to test surfaces situated in such a hostile environment, it is therefore necessary to use remote-controlled machines.

Use of remote-controlled video cameras is known for supplying video images of the surface under test.

Unfortunately that technique is insufficient for accurately determining and/or characterizing certain details of the surface under test, e.g. the existence of defects or indications as to their existence. The operator measures various distances directly on the screen or via video measuring apparatus, which distances are then transformed by calculation, e.g. so as to determine the position and the dimensions of the indication in question. A first drawback is that if the surface under test is complex, the calculation can become very tedious. Furthermore, if the indication to be analyzed is large and is therefore distributed over a plurality of video images, it can be very difficult to join them up, giving rise to random accuracy in calculated dimensions.

Furthermore, since the mobility of the camera can be limited, and therefore its camera angles can be limited, it can be difficult or even impossible to use the video image. Moreover, it may be impossible to obtain an overall picture of the entire surface under test on a single image, depending on the geometrical shape of said surface.

OBJECTS AND SUMMARY OF THE INVENTION

An object of the invention is to provide a method of testing a surface non-destructively, in particular in a hostile environment, which method does not suffer from the above-mentioned drawbacks.

Therefore, an object of the invention is to provide a method of testing a surface, in particular in a hostile environment, which method makes it possible to characterize and/or to analyze simply and reliably any indications present on the surface under test.

Another object of the invention is to provide a method of testing a surface, in particular in a hostile environment, which method guarantees optimum accuracy in characterizing such indications.

A further object of the invention is to provide a method of testing a surface, in particular in a hostile environment, which method makes it possible to represent the surface under test and/or the indications to be characterized in any desired manner, in particular using different camera angles and different configurations (overall view or fragmentary views), and also makes it possible to compare different images obtained in this way.

Another object of the invention is to provide a method of testing a surface, in particular in a hostile environment, in which method the characterization calculation on the basis of the distances measured on the video image is performed automatically, thereby freeing the operator from a task that is lengthy, tedious, and uninteresting.

The invention achieves these objects and others by providing a method of testing a surface non-destructively in particular in a hostile environment, the method including the following step:

disposing a remote-controlled video camera in the vicinity of said surface, said video camera being supported by an instrumented positioning device, and being used to supply video images of said surface under test;

said method further including the following steps:

synthesizing a three-dimensional image of a model of said surface under test;

superposing one or more two-dimensional projections of the synthesized image on one or more corresponding video images on a screen;

calibrating one or more two-dimensional projections of said synthesized image on one or more corresponding video images so as to obtain a synthesized image substantially corresponding to the surface under test;

transferring one or more indications visible in the corresponding video image onto a calibrated two-dimensional projection of said synthesized image, and then projecting the indications onto the three-dimensional synthesized image; and processing the resulting three-dimensional image(s), or their two-dimensional projections, so as to analyze and characterize said indications on the surface under test.

Generally, the step of synthesizing an image is performed by entering into software input parameters that are characteristic of said surface. Thus, the surface under test can be described mathematically and an indication situated in said surface under test can be characterized, i.e. dimensioned and positioned with improved accuracy by means of the method of the invention.

In an advantageous variant of the method, the step of superposing a synthesized image on a corresponding video image is performed by superposing the synthesized image as a whole on the video image.

In another variant of the method, the step of superposing a synthesized image on a corresponding video image is performed by superposing the synthesized image manually point-by-point on the video image.

Preferably, the step of calibrating a synthesized image on a corresponding video image is performed by causing accurately known elements to coincide, and/or by causing one or more of said input parameters to vary.

Optionally, the step of transferring one or more indications from the video image onto a synthesized image may be performed by point-by-point manual transfer.

However, the step of transferring one or more indications from the video image onto a synthesized image may also be performed by a contour extraction method.

Advantageously, the step of processing the synthesized image(s) includes in particular accurately positioning the indication, accurately dimensioning the indication, modifying the camera angle, comparing different views of the same indication, re-constituting a large indication, re-constituting three-dimensionally the entire tested surface, storing one or more images, and printing them out.

Preferably, the software is three-dimensional computer-aided design [CAD] software.

In a particular application of the invention, the method is used for analyzing and characterizing indications shown up by performing dye penetration testing on welds, in particular welds by means of which adapters are welded to a cover of a nuclear reactor vessel, where said input parameters for synthesizing an image of the surface under test include in particular the dimensional parameters of the cover, of the adapter, and of the weld, the position parameters of the device for positioning the video camera, the parameters of one or more optional mirrors, and the operating parameters of the video camera.

BRIEF DESCRIPTION OF THE DRAWINGS

Other characteristics and advantages of the invention appear from the following detailed description of an implementation of the invention, given by way of non-limiting example and with reference to the accompanying drawings, in which.

MORE DETAILED DESCRIPTION

Figure 1:
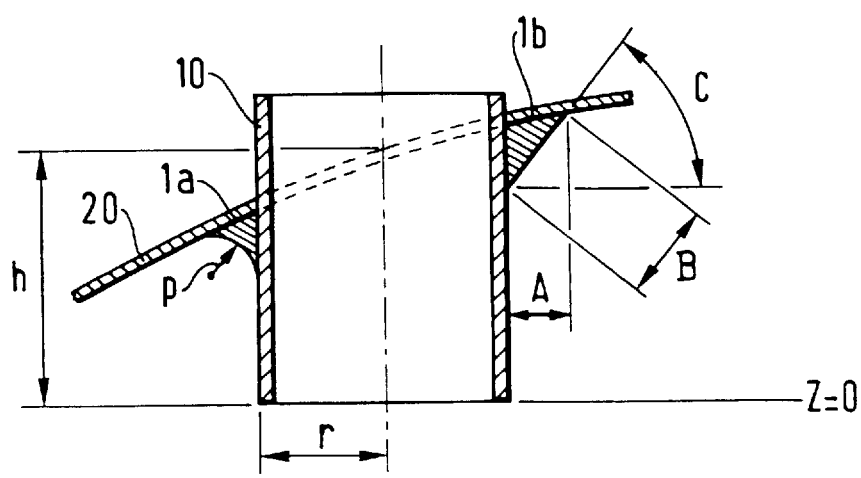
FIG. 1 is diagrammatic vertical section view showing how an adapter is welded to the cover of a nuclear reactor vessel.

The method of the invention is described below with reference to a particular application, namely that of characterizing indications shown up by dye penetration testing performed on welds, in particular welds by means of which a vent and adapters are welded to the covers of nuclear reactor vessels.

Since such welds are subjected to considerable stresses, in particular because of the temperature and pressure conditions inside a vessel, they become worn as time passes, and indications, i.e. defects, e.g. cracks, can appear. Dye penetration testing is a technique that makes it possible to show up such indications. Firstly, the welds are cleaned, in particular by brushing, so as to remove any traces of oxidation, and then a wetting agent is applied to the weld. The wetting agent infiltrates into the smallest cracks in the weld. After a certain infiltration time, a masking agent acting substantially as a blotter is applied. The wetting agent that has infiltrated into the indications is thus absorbed, and it leaves characteristic marks marking said indications. By analyzing the characteristics of the indications, i.e. in particular their shapes and their dimensions, it is possible to determine the general state of the weld.

It is not possible to use a man to characterize such indications first hand, because the man used would, within a few minutes, be subjected to the maximum authorized annual radiation.

It is therefore necessary to use machines that are remote controlled and/or that are instrumented from outside by an operator.

In accordance with the invention, a video camera is disposed inside the cover of the vessel so as to supply video images of the surfaces under test, i.e. of the welds. The method of the invention may be used for any of the welds inside said cover, but its results are more spectacular with the most complex surfaces, i.e. with the adapter welds which are eccentric relative to the central vertical axis of the cover. Such an adapter 10 is shown in FIGS. 1 to 4.

The video camera is disposed on a instrumented positioning device, such as a robot, which enables the operator to displace said camera in any desired manner from the operator's work-station, and to know accurately the exact position of said camera at any time.

The method of the invention improves and simplifies processing of the video images supplied by the camera.

To this end, in accordance with the invention, a three-dimensional image is synthesized of the surface under test, i.e., with reference to the figures, the weld 1 by means of which an adapter 10 is welded to a cover 20 of a nuclear reactor vessel. The image is preferably synthesized by means of three-dimensional computer-aided design (3D CAD) software, or robotics CAD software, on the basis of known input parameters.

The synthesized image, which represents an ideal (i.e. theoretical) model of the weld is then superposed on a corresponding video image, and said input parameters are modified so as to calibrate and re-adjust the synthesized image on the video image. A synthesized image of the weld is then obtained that corresponds very accurately to the weld itself.

Any indications visible on the video image are then transferred onto the synthesized image, and the synthesized image can then be processed as desired by means of CAD.

Many input parameters make it possible to synthesize an image.

With reference to FIG. 1, a weld by means of which an eccentric adapter 10 is welded to a spherical cover 20 includes a "narrow" end 1a where the surface of the weld has a circular curve, and a "wide" end 1b where the surface of the weld is substantially plane. Said parameters of the weld then include in particular the radius p of the narrow end 1a of the weld, the angle C of the plane of the wide end 1b of the weld relative to the horizontal, the width A, in the horizontal plane, of the wide end 1b of the weld, and the length B, in its own plane, of the wide end 1b of the weld.

Figure 2:
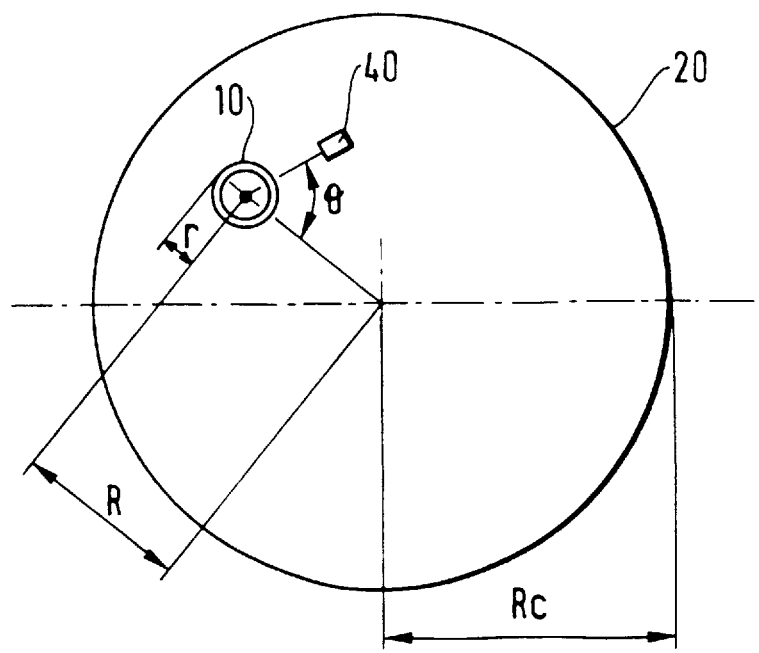
FIG. 2 is a diagrammatic horizontal section view showing a video camera and the cover of the vessel with an adapter.

As shown in FIGS. 1 and 2, the input parameters also include the dimensions of the cover and of the adapter, i.e. the radius Rc of the cover, the outside radius r of the adapter, and the height h of the adapter relative to the cover.

The surface to be analyzed is thus known mathematically, as is its three-dimensional position.

In order to obtain a synthesized image that is compatible with the video image supplied by the video camera, other parameters need to be taken into account.

Figure 3:
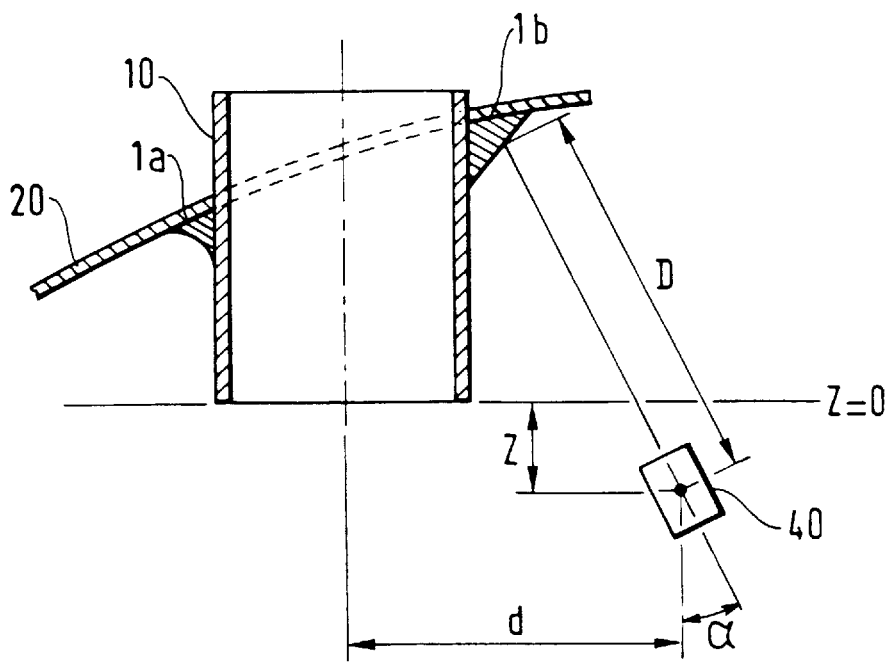
FIG. 3 is a view similar to FIG. 1, further showing a video camera.
Figure 4:
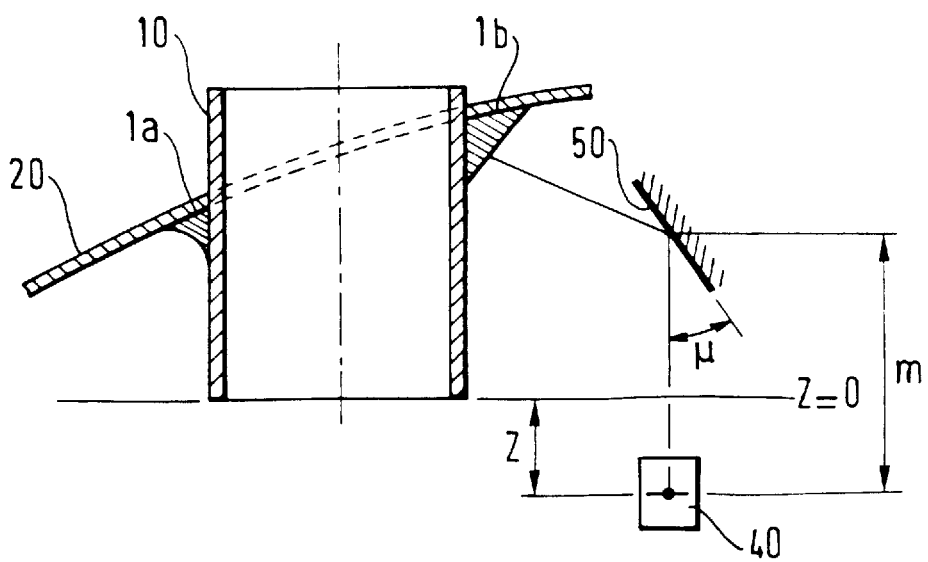
FIG. 4 is a view similar to FIG. 3, further showing a rectifying mirror.

With reference to FIGS. 3 and 4, such parameters include in particular the position parameters of the robot carrying the camera 40, i.e. the distance Z between the camera and the horizontal plane of the bottom end of the adapter, the lateral offset d of the camera, the elevation angle $\alpha$, and the camera angle $\theta$. When one or more rectifying mirrors 50 are used, as shown in FIG. 4, the input parameters also include the distance m between said mirror and the center of the camera 40, and the angle $\mu$ of the mirror relative to the vertical.

The input parameters also include the operating parameters of the camera, e.g. the convergence distance D of the camera.

The characteristics of the video camera are thus also known mathematically, as is its three-dimensional position.

On the basis of all of the input parameters, the CAD software calculates an image as ought to be seen by the camera. This is the synthesized image.

The synthesized image, or three-dimensional model, thus includes in particular the inside sphere of the cover, the cylinder representing the adapter, the surface representing the weld, the cover-weld intersection curve, and the adapter-weld intersection curve. Generally, when testing the welds, the zones adjacent to the weld by means of which the adapter is welded to the cover are also inspected. The synthesized image therefore advantageously also includes the inspection limit curve on the cover and the inspection limit curve on the adapter.

Since the resulting three-dimensional synthesized image is an ideal picture of the zone under test, in accordance with the invention said synthesized image is calibrated on the real images so as to obtain a faithful three-dimensional picture of the surface under test.

For this purpose, one or more two-dimensional projections of the synthesized image are superposed on one or more corresponding video images on a screen. The video images may be of two types: images of the weld after cleaning but prior to dye penetration testing, and images of the weld after dye penetration testing.

For the superposition and calibration steps, the images prior to dye penetration testing are preferably used.

A synthesized image may be superposed on a video image on a screen either as a whole, or point-by-point as a function of the hardware used, the whole-image superposition method generally being preferred.

In order to calibrate the synthesized image, the above-mentioned input parameters of the synthesized image are modified so that the elements that are known accurately are caused to coincide. For this step, a plurality of video images and a plurality of two-dimensional projections of the synthesized image may be used.

After calibration, a three-dimensional synthesized image is obtained that faithfully represents the surface of the weld.

Any indications that are visible on the video image(s) after dye penetration testing can then be transferred to two-dimensional projections of the synthesized image by entering suitable parameters into the CAD software.

The indications visible on the video images may be transferred manually point by point at some significant points along a curve, e.g. circles or ellipses, or by a contour extraction method.

The indications can then be analyzed on the two-dimensional projections of the synthesized image so as to determine their positions and their dimensions.

A particularly advantageous aspect of the invention is that by using 3D CAD it is possible to form a model of said indications on a three-dimensional synthesized image by projecting the two-dimensional indications onto the three-dimensional model.

All of the characteristics of the 3D CAD software can then be used to modify the camera angle, to remove obstacles to observation, to dimension the indication(s) accurately by taking into account the complexity of the surface, and to position the indication(s) accurately.

Since these operations are performed for each video image, it is possible to re-constitute three-dimensionally the entire tested surface. It is also possible to re-constitute a large indication by merging indications that are visible on various video images. It is also possible to compare different information obtained by various images being shot of the same indication, and by choosing the most plausible image. Likewise, it is possible to output screen copies so as to include both overall views from different angles, and also fragmentary views in the test report.

The method of the invention for characterizing indications by means of synthesized images makes it possible to supply an inspection report which gives for each indication its type (e.g. linear or elliptical), its three-dimensional position, and its dimensions. This data and the corresponding synthesized images and video images may also be archived for the purposes of comparison during a future test.

In the above description, reference is made to a video camera. Naturally, the video camera is part of a video system that may in particular include one or more video cassette recorders for the images before and after dye penetration testing, a video monitor, video measuring apparatus, and a video printer.

The invention is described with reference to the welds by means of which an adapter is welded to the cover of a nuclear reactor vessel, but it is also applicable to non-destructive testing of any surfaces situated in any hostile environment or in an environment that is not easily accessible or that is inaccessible to man.

I claim:

1. A method for testing a surface for defects non-destructively, comprising the steps of:

(a) disposing a remote-controlled video camera in the vicinity of said surface for supplying video images of said surface, said video camera being supported by an instrumented positioning device;

(b) using known input parameters to synthesize a three-dimensional synthesized image representing an ideal model of said surface;

(c) superimposing a two-dimensional projection of the synthesized image onto a corresponding video image to obtain a superimposed image;

(d) calibrating said synthesized image so as to overlap the corresponding video image to obtain data representing a calibrated image substantially corresponding to the surface;

(e) transferring a defect image from said corresponding video image onto the calibrated image to obtain data representing a two-dimensional projected image of the defect; (f) projecting the two-dimensional projected image of said defect image onto said three-dimensional synthesized image of said surface to obtain data representing a three-dimensional resultant image which substantially corresponds to the surface; and (g) processing the data of the three-dimensional resultant image so as to analyze and characterize said defect image of the surface.

2. A method according to claim 1, wherein step (b) is performed by inputting the parameters into a computer program to thereby describe said surface mathematically.

3. A method according to claim 1, wherein said step (c) is performed by superimposing the synthesized image as a whole on the video image.

4. A method according to claim 1, wherein said step (c) is performed by superimposing the synthesized image manually point-by-point on the video image.

5. A method according to claim 1, wherein said step (d) is performed by modifying said input parameters to cause the synthesized image to overlap the video image so as to obtain data which more accurately represent the actual surface.

6. A method according to claim 1, wherein said step (e) is performed by a point-by-point manual transfer.

7. A method according to claim 1, wherein said step (e) is performed by a contour extraction method.

8. A method according to claims 1, wherein said step (g) comprises:

(g1) accurately positioning said defect image, (g2) accurately dimensioning said defect image, (g3) modifying the camera angle, (g4) comparing different views of the same defect image, (g5) re-constituting a large version of said defect image, (g6) re-constituting three-dimensionally the surface, (g7) storing said defect image, and (g8) printing said defect image.

9. A method according to claim 2, wherein said software is a three-dimensional computer-aided design software.

10. The method according to claim 1, wherein said surface is wet with a penetrating dye prior to supplying the video images so as to enhance said defect image.

11. A surface defect testing method, as recited in claim 2, wherein said surface is a part of a nuclear reactor vessel, and wherein said input parameters comprise:

ideal dimensional parameters of a cover of the nuclear reactor vessel, an adapter of the nuclear reactor vessel, and a weld applied to connect the adapter to the cover;

position parameters of the instrumented positioning device for positioning said video camera;

operating parameters of said video camera.

12. The method according to claim 10, wherein a masking agent is applied to said defect after the surface has been wet by the penetrating dye.

\* \* \* \* \*